United States Patent [19]

Kirkpatrick, Jr. et al.

[11] Patent Number: 5,194,910
[45] Date of Patent: Mar. 16, 1993

[54] USE OF OPTICAL SPECTROMETRY TO EVALUATE THE CONDITION OF USED MOTOR OIL

[75] Inventors: James F. Kirkpatrick, Jr.; James R. Stevenson, both of Oak Ridge, Tenn.

[73] Assignee: Gas Research Institute, Chicago, Ill.

[21] Appl. No.: 561,452

[22] Filed: Jul. 31, 1990

[51] Int. Cl.$^5$ .................... G01N 33/28; G01N 21/88
[52] U.S. Cl. ...................... 356/70; 356/440; 356/441; 356/320; 356/326; 356/435; 250/563; 250/573; 73/53.05
[58] Field of Search ................ 356/70, 38, 440, 441, 356/442, 320, 326, 335, 435, 436, 320, 407; 250/563, 564, 573, 577; 73/53.05

[56] References Cited

U.S. PATENT DOCUMENTS

| | | |
|---|---|---|
| 1,940,772 | 12/1933 | Schoenberg . |
| 2,889,736 | 6/1959 | Borg . |
| 3,371,574 | 3/1968 | Dwyer . |
| 3,790,279 | 2/1974 | Skala . |
| 3,892,485 | 7/1975 | Merritt et al. . |
| 3,910,701 | 10/1975 | Henderson et al. ............ 356/446 |
| 4,003,661 | 1/1977 | Yamano . |
| 4,492,461 | 1/1985 | Jones et al. . |
| 4,929,347 | 5/1990 | Yamazoe et al. ............ 356/436 |

FOREIGN PATENT DOCUMENTS 0264238 6/1991 Japan ..................... 356/70

OTHER PUBLICATIONS

Jay Janzen, Extinction of Light by Highly Nonspherical Strongly Absorbing Colloidal Particles . . . ; Sep. 1, 1980/vol. 19, No. 17/Applied Science.

Masuhiko Kawamura et al. Electron Microscopic Observation of Soots in Used Diesel Engine Oils, Jul., 1987 Lubrication Engineering.

George Murphy, MBCA Oil Analysis Program: Five Years Later, Smoky Mountain Section.

Rwon et al., Condition Monitoring for an Internal Combustion Engine, Jun., 1987 Butterworth & Co. Ltd.

N. A. Graham, By-Pass Lube Oil Filtration, Int'l Congress and Exposition, Detroit, Mi., Feb. 24-28, 1986.

N. K. Myshkin et al., Survey of Methods for Measuring Oil Contamination in Wear, Institute of Mechanics of Metal-Polymer Systems, Byelorussian SSR Academy of Sciences, Gomel, U.S.S.R. May, 1986, Jun. 1987.

R. W. Erickson et al., Rapid Oil Analysis, vol. 70, No. 2, 1984, Lubrication Braham Prakash, et al., A New Device for Monitoring of Contaminants in Engine Lubricating Oils, 4th Tribology Conference, Budapest, Hungary, Journal of Condition Monitoring, Sep. 22-24, 1987.

(List continued on next page.)

Primary Examiner—Vincent P. McGraw
Assistant Examiner—LaCharles Keesee
Attorney, Agent, or Firm—Luedeka, Hodges, Neely & Graham

[57] ABSTRACT

Methods and apparatus employing optical spectrometry techniques to measure metallic wear debris contamination in used motor oil, even in the presence of carbon particulates. Measurement results based on optical spectrometry as disclosed herein correlate closely with results of laboratory analysis based on atomic spectrometry. Variation in transmittance of a sample of oil as a function of wavelength within the approximate range of 300 nm (violet) to 1300 nm (near-infrared) is measured as an indicator of metallic wear debris contamination. Conveniently, measurements may be taken at just two wavelengths within the range, for example 565 nm (green) and 660 nm (red). The ratio of transmittance at the shorter of the two wavelengths to transmittance at the longer of the two wavelengths is determined as an indication of the amount of metallic wear debris contamination, decreases in the ratio from a ratio of unity indicating increasing levels of contamination. Oil degradation not necessarily accompanied by metallic wear debris contamination may also be measured.

25 Claims, 6 Drawing Sheets

OTHER PUBLICATIONS

Jim C. Fitch, Theory Design and Performance Characteristics of a Direct-Reading Portable Solid Contaminant Analyzer, Earthmoving Industry Conf. Peoria, Ill., Apr. 8-10, 1986.

Barry M. Verdegan, et al., Lubricating Oil Condition Monitoring Through Particle Size Analysis, Truck and Buss Meeting and Exp. Indianapolis, Ind. Nov. 7-10, 1988.

A. D. Stuart, et al., Spectroscopic Measurement of used Lubricating Oil Quality, vol. 43, No. 1, 1989, Applied Spectroscopy.

P. A. Asseff, Used Engine Oil Analyses-Review, Fuels and Lubricants Meet. Tulsa, Jun. 7-9, 1977.

Shirley E. Schwartz et al., Development of an Automatic Engine Oil-Change Indicator System, Int'l Congress & Exp., Detroit, Mi., Feb. 23-27, 1987.

USE OF OPTICAL SPECTROMETRY TO EVALUATE THE CONDITION OF USED MOTOR OIL

BACKGROUND OF THE INVENTION

The present invention relates generally to the testing of used lubricating oil, such as lubricating oil in an internal combustion engine and, more particularly, to optical methods and apparatus for evaluating the condition of lubricating oil to determine whether the oil should be changed.

It is well known that the life expectancies of internal combustion engines are heavily influenced by the rate of wear of lubricated surfaces. When good lubricating oil quality is maintained, small automotive engines may exceed 5,000 hours (equivalent to about 150,000 miles) of operation with virtually no wear. At the other extreme, engines run with badly contaminated oil wear rapidly and may fail before even a small fraction of the potential engine life is realized.

Although most engine users realize that engine life is directly tied to maintaining good oil quality, there is much less certainty concerning what is good oil quality and how good oil quality should be maintained. Most engine manufacturers recommend fixed oil change schedules based on elapsed time, elapsed vehicle miles, and/or elapsed hours of oil use. However, it is well known that oil life is a complex function of operating conditions, weather, engine condition, and time-in-use, as opposed to a fixed mileage or time.

Thus, many sophisticated large engine operators such as the military, railroads and some fleet operators rely on periodic in-service oil analysis rather than fixed oil change intervals so that oil is changed only when it is degraded. The key analysis method used for reciprocating engines is atomic spectrometry. This technique involves atomizing (burning) the oil sample and then measuring either absorption or emission of specific wavelengths of ultraviolet radiation associated with elements which may be present in the oil as a result of wear. The technique provides information about both the quantity and species of debris elements present in the oil. Results are usually reported in parts per million of wear metals by weight. When oil-wetted engine metals are reported in the used oil which were not present in the original oil, it is assumed that they are the result of wear. A full oil analysis not only provides information about the quality of the oil, but also gives the operator insight into the condition of the engine from which the oil sample was taken.

Unfortunately, laboratory oil analysis is expensive and may not always be cost-effective for small engine users. Accordingly, a variety of lower-cost approaches have been proposed, many optically based. Simple measurement of light attenuation by an oil sample is disclosed, for example, in Schoenberg U.S. Pat. No. 1,940,772, Borg U.S. Pat. No. 2,889,736 and Yamano U.S. Pat. No. 4,003,661. A more sophisticated system, which is said to measure wear debris contamination independently of changes in color or opacity, is disclosed in Merritt et al U.S. Pat. No. 3,892,485 and employs two separate detectors for respectively measuring attenuation and scattering of light from a source applied to a volume of oil. The attenuation measurement is employed in a feedback loop to vary the intensity of the light source as compensation for changes in opacity. Another system, disclosed in Skala U.S. Pat. No. 3,790,279, similarly employs separate light scattering and light attenuation measurements. A calculation based on these separate measurements is said to provide an indication of contamination.

Other optically-based approaches have been proposed. Miller et al U.S. Pat. No. 3,049,964 discloses a method for detecting impurities wherein a drop of oil is applied to filter paper. Solid material remains in the center as a dark spot, while oil spreads. A light bulb illuminates the filter paper and spot, and measurement of reflected light indicates the size of the dark spot of impurities. A technique known as "Ferrography" is disclosed in Jones et al U.S. Pat. No. 4,492,461.

Nevertheless, there remains a need for a low-cost technique and instrument for accurately detecting metallic wear debris in used oil, such as used motor oil, particularly in the presence of high levels of carbon particulate.

By way of further background, discussed below in detail are characteristics of lubricating oil, a number of specific wear mechanisms, the significance of wear rate being nonlinear with respect to time, and reasons why metallic wear debris concentration is a good indicator of a decrease in oil quality.

Oil is used to prevent direct contact between opposing metal surfaces which are in motion relative to one another. In essence, the normal load between the surfaces is supported by the liquid, thereby minimizing shear forces. In addition, modern motor oils contain anti-wear additives which modify the metal surfaces, resulting in lower levels of friction and wear than could be provided by the base oil stock alone. Significant wear normally occurs only when the oil and/or additives are allowed to degrade.

The ability of a lubricating oil to prevent wear is impaired by the presence of contaminates. Solid particles in the oil cause wear by simple mechanical contact with oil-wetted surfaces, by increasing effective oil viscosity, and by disrupting hydrodynamic films. In the case of very small (sub-micron-sized) particles, wear results from mild abrasive (erosive) action. However, when a particle reaches the oil thickness dimension between opposing, moving surfaces, catastrophic wear results from galling and disruption of oil films. Large metal particles are gouged providing a higher level of large particle contamination. Once a critical large particle population is reached, this cycle becomes self-accelerating and wear rates increase exponentially until the oil is changed or the machine fails.

Liquid contaminates are also of concern. Water exposed to oxides of sulfur and nitrogen formed in combustion processes forms acids. Oxidation of the oil results in viscosity increases accompanied by reduced flow rates and decreased convective heat transfer. Eventually, tars and lacquers form, further blocking heat transfer, blocking filters, and restricting oil flow in narrow passages.

In reciprocating, internal-combustion engines, oil degradation rates are relatively high due to the exposure of the oil to the combustion process. A fundamental cause of oil contamination in engines is the buildup of small, elemental, carbon particulates in the oil. In low concentrations these particles are relatively harmless. However, once concentration levels are sufficient to allow agglomeration, the particles bind together. The rate with which the particles are formed by combustion is primarily a function of the carbon fraction of the fuel, with very high deposition rates in diesels and much lower rates in natural-gas-fueled engines. Other fuel-dependent contaminates include sulfur, lead and water. Other causes of lubricating oil degradation which are exacerbated in reciprocating engines include exposure to condensation, fuel dilution, and the existence of high oil shear rates. As noted above, the engine-dependent factors which promote oil degradation are not constants and vary with engine service environment, engine condition, and engine design.

There are a number of specific wear mechanisms which apply to reciprocating engines, as discussed in the next several paragraphs.

Adhesive wear occurs when direct, "dry" contact is allowed between the opposing metal surfaces. Such contact results in severe friction heating and ultimately in adhesion (seizure) of opposing surfaces. This type of wear typically results from an interruption of the oil supply such as when a hot engine is shut-off: the hot, thin oil drains from lubricated surfaces; it cools overnight, becoming viscous; and finally, the engine is started with only residual lubrication from the remaining oil and anti-wear coatings. The amount of damage done is determined by a race between the rate of removal of the anti-wear coating and the arrival of the thick, slow-moving oil. Obviously, damage will be severe if the anti-wear additives have been exhausted or the low-temperature oil viscosity has increased.

A secondary effect of adhesion is to contaminate the oil with work-hardened wear debris and to roughen the metal surfaces, causing abrasive wear not only at starting but for hours afterward.

Abrasive wear, mentioned above, occurs when the thickness of the oil film which separates moving surfaces is exceeded by the dimensions of solid particles suspended in the oil or the height of surface protuberances (asperities) on the opposing surfaces. This wear mechanism is similar to the familiar action of abrasive papers or grinding wheels, material removed from one or more of the opposing surfaces by localized, intermittent contact. Abrasive wear rates increase with decreasing oil viscosity or increasing particle size or concentration. Lower oil viscosities lead to thinner lubricating films, while large, coarse particles remove material more rapidly than small, fine particles.

Erosive wear occurs when particle-laden oil impinges on a surface. Material is removed from the surface by the scouring action. As is the case with abrasive wear, a key factor in reducing erosive wear is maintaining a clean, particle-free oil.

Surface fatigue results from cyclic normal loading (vibration) of the metal surfaces rather than sliding friction. Cam-follower surfaces are subject to this type of wear which results in pitting of the surfaces. Again, particle contamination provides a source of higher point loading, aggravating wear.

Corrosive wear is the loss of material as a result of chemical modification of the oil-wetted surfaces. Acids form in engine lubricating oils as a result of exposure to combustion byproducts and condensate moisture. In general, the presence of acids in a lubricating oil will weaken metal surfaces, making them much more vulnerable to mechanical wear. Motor oils contain sacrificial additives to combat corrosion. Once they are consumed, the rate of corrosive wear escalates.

In addition, both the base oil and the anti-wear additives are susceptible to changes in molecular structure at high temperatures. In the case of the base oil, oxidation results in viscosity increases, particulate formation, and solid deposits known as lacquer. Motor oils contain sacrificial additives to control oxidation. However, oxidation rates may also be increased by the catalytic action of metallic wear debris accumulating in the oil.

A key point is that most of the wear processes are not linear with respect to time, and it is correspondingly significant that oil quality does not degrade in uniform fashion across engine types or even in a single engine as it ages. Typically, wear remains at very low levels during most of the oil's useful life, and then drastically increases as one or more of the additives are depleted. This nonlinear wear rate is one of the primary reasons for being very conservative in selecting an oil change interval; if one misjudges, a great deal of wear will take place in a relatively short interval. Most engine manufacturers suggest that engine oil be changed on a periodic basis dictated by the elapsed engine operating hours or vehicle miles since the last oil change. However, in view of the wide variation in oil degradation rates, this is questionable practice.

By the same token, it is folly to attempt to maintain oil quality on the basis of infrequently conducted tests. Tests must be conducted more frequently as the oil ages, and results should be trended to detect the onset of the increase in wear.

The best measure of the lubricating quality of an oil is the absence or presence of wear. By definition, if wear is not occurring, then the machine is well-lubricated. Thus, wear debris concentration is an objective test of the primary oil function, i.e., prevention of wear. If wear debris is not present in the oil after a period of residence in the engine, then it is axiomatic that the oil is providing adequate lubrication and need not be changed. The presence of wear can be detected by examining the used engine oil for the presence of wear debris. If the oil is of good quality and not degraded, wear debris levels will remain very low. If, on the other hand, the oil is badly degraded, wear debris levels will increase, as will the mean particle size of the debris.

Figure 1:
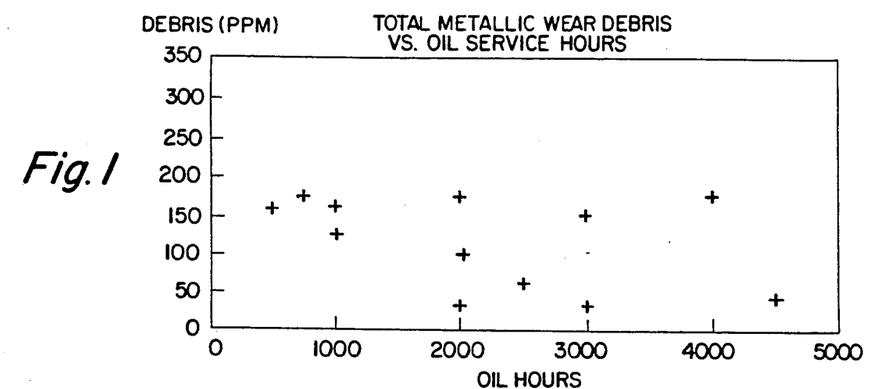
FIG. 1, referred to above, is a plot of engine wear debris as a function of engine operating hours for a plurality of motor oil samples from natural-gas-fueled engines, demonstrating little or no relationship between oil service time and lubricating quality.
Figure 2:
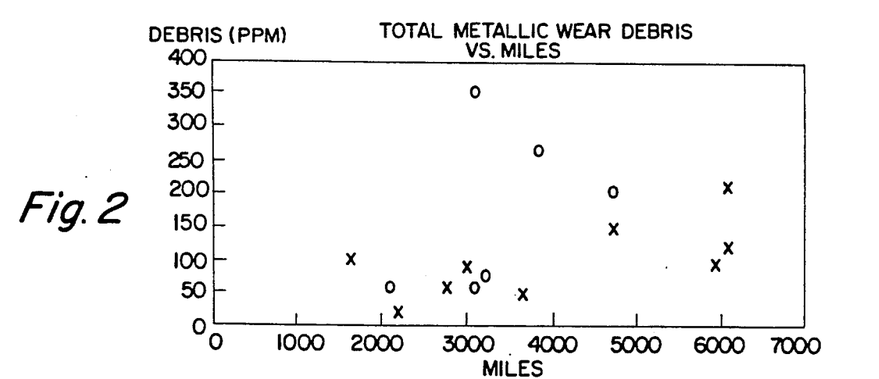
FIG. 2, also referred to above, is a similar plot of total wear debris as a function of vehicle mileage for a plurality of motor oil samples from gasoline-fueled engines, likewise demonstrating a lack of correspondence between mileage and lubricating oil quality.

Illustrating these points, FIGS. 1 and 2 are plots of total wear debris levels in randomly sampled engine oils as a function of engine operating hours and engine miles, respectively, since the last oil change. From these plots, it can be seen that there is little or no relationship between oil service time and oil lubricating quality, demonstrating the problems with oil change intervals based on service time measures. It may be noted that the data shown in FIG. 1 is based on oil samples from engines fueled with low-carbon-fraction natural gas, which is primarily methane (1:4 carbon/hydrogen ratio). The oil samples on which FIG. 1 is based are various SAE 10W-30, 30 and 40 motor oils. FIG. 2 is based on oil samples from engines fueled with gasoline (7:16 carbon/hydrogen ratio). In FIG. 2, the "x" sample points are for SAE 20W-50 oil, and the "o" sample points are from SAE 10W-30 oil.

Most small machine and automotive oil maintenance programs are based on periodic oil changes. However, from the foregoing it will be appreciated that oil changes based on fixed service intervals are a questionable maintenance practice. The optimal oil maintenance program is one in which oil changes are triggered by the results of an evaluation of oil condition, not the passage of an arbitrary service period.

SUMMARY OF THE INVENTION

Accordingly, it is an object of the invention to provide a technique and instrument for providing an objective, immediate and inexpensive measure of lubricating oil quality.

It is a related object of the invention to provide an instrument which can be employed on a frequent and regular basis.

It is another object of the invention to provide an instrument which is hand-held and battery-powered or which can be used for continuous on-line monitoring of oil condition in an engine.

Briefly, and in accordance with an overall aspect of the invention, it is recognized that optical spectrometry techniques can be employed to determine metallic wear debris contamination in used motor oil, even in the presence of carbon particulates.

Thus, in accordance with the invention, variation in transmittance of a sample of oil as a function of wavelength is measured as an indicator of oil lubricating characteristics. In other words, if transmittance is plotted as a function of wavelength, the slope of the resultant plot is an indicator of oil lubricating characteristics. Variation in transmittance as a function of wavelength preferably is measured within an approximate wavelength range of from 300 nm (violet) to 1300 nm (near-infrared), but measurements need not encompass that entire range.

Measurement of variation in transmittance as a function of wavelength is believed to primarily indicate metallic wear debris contamination, with an increasing slope in a plot of transmittance as a function of wavelength indicating an increasing level of metallic wear debris contamination. However, the technique of the invention also indicates other degradations in lubricating oil quality, such as what is believed to be a buildup of large polymer structures as a result of heating of the oil. Such degradations resulting in decreasing oil lubricating quality are also reflected in an increasing slope in a plot of transmittance as a function of wavelength.

It will be appreciated that a variety of techniques may be employed to measure and evaluate the transmission spectrum to determine lubricating oil quality such as metallic wear debris concentration, including computerized pattern analysis.

However, in accordance with the invention, a low-cost yet highly effective technique is employed. In particular, measuring elements are employed to optically measure transmittance at just two distinct wavelengths within the approximate wavelength range. For example, any of the following wavelength pairs may be employed: 565 nm (green) and 660 nm (red); 565 nm (green) and 700 nm (red); 660 nm (red) and 880 nm (infrared); 440 nm (blue) and 700 nm (red); and 660 nm (red) and 940 nm (near-infrared). As a further example, a wavelength pair in the near-infrared range can be employed, for example 940 nm and 1300 nm.

After measuring transmittance at two distinct wavelengths to determine variation in transmittance as a function of wavelength, a variety of calculation techniques can be employed to determine the amount of metallic wear debris contamination. In one embodiment, a calculating element is connected to the measuring elements and is operable to calculate the ratio of transmittance at the shorter of the two distinct wavelengths to transmittance at the longer of the two distinct wavelengths as an indication of the amount of metallic wear debris contamination. For example, the ratio of transmittances of 565 nm (green) and 660 nm (red) light is calculated. Decreases in this ratio from a ratio of unity indicate increasing contamination.

Typically the measuring elements comprise a pair of light-emitting elements, such as light-emitting diodes (LEDs) or laser diodes, respectively operating at the two distinct wavelengths, and a pair of light sensors such as photoconductors respectively corresponding to the light-emitting elements. A sample delivery device presents a sample of oil to be measured between the light-emitting elements and the corresponding light sensors such that the amount of light reaching each of the light sensors depends upon the transmittance of the oil sample at a corresponding one of the wavelengths.

Preferably, diffused light is employed for the transmittance measurements. Two different approaches may be employed for providing the diffused light. In one approach, colored plastic diffusers are positioned between the light-emitting elements and the sample delivery device, and between the sample delivery device and the light sensors. In another approach, diffused light may be achieved simply by providing a cellulose matrix, such as filter paper, carrying the oil sample.

The sample delivery device includes means for presenting the oil sample for transmittance measurements as a relatively uniform thin film. In one embodiment, the sample delivery device includes a pair of transparent plastic strips facing each other and spaced apart by spacers each having an aperture for receiving an oil sample. Alternatively, the sample delivery device may simply comprise the cellulose matrix, such as filter paper, as described above in the context of a light diffuser.

Accordingly, low-cost optical tests in accordance with the invention can be used to screen motor oils in engines fueled with natural gas or gasoline. These tests produce results which closely correlate with wear debris concentrations as determined by atomic spectrometry. Moreover, these tests can be performed by untrained personnel in the field with no special equipment other than a relatively inexpensive, hand-held, battery-powered instrument in accordance with the invention.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

DETAILED DESCRIPTION OF THE PREFERRED EMBODIMENTS

As discussed under the heading "Background of the Invention" above, wear debris size and concentrations are intimately related to wear rates. A machine with good lubrication and no vibration or alignment problems produces only very low concentrations of very fine wear debris, with mean particle sizes on the order of 0.1 microns or smaller. The normal carbon particulate size range resulting from combustion is even smaller, on the order of 20 to 30 nm. Particles of this size scatter and absorb visible light. Consequently, light transmission measurements can indicate the concentration of the particles in the oil.

Conductive materials such as elemental metals both scatter and absorb light when present as particles in a liquid. The combined effect of scattering and absorption is known as extinction, which is simply the reduction in the intensity of light transmitted through the medium. Extinction is typically expressed as the ratio of light transmitted through the medium to the light incident on the medium.

Light transmission through a clear liquid laden with particles can be described by a product of the following form:

$$T = T_o * Exp(-n1*a1*Q1*t) * Exp(-n2*a2*Q2*t) \ldots$$

where T is the magnitude of the transmitted light; To is the intensity of the incident light (source); n(1,2, ... ) is the number of particles per unit volume of the medium; a(1,2, ... ) is the mean particle surface area (normal and parallel to path axis for the subject instrument); Q is the total extinction per unit of flux incident on a particle; and t is the length of the light path through the oil. Ideally a product term should be used to describe each particle size range and species.

The parameter Q is a complicated function which is derived from consideration of the incident and scattered electric fields, typically called Mie and Rayleigh scattering theory. In essence, the parameter Q relates particle size, complex refractive index of the material, refractive indices of the particle and of the medium (oil), and the frequency or wavelength of the light to the extinction efficiency. Typically, with respect to particles of interest, extinction efficiency rapidly increases with particle size (Rayleigh scattering) until the wavelength of the light is approached. At that point the efficiency becomes asymptotic with a constant value of 2 after minor perturbations for absorptive materials (such as metals and carbon) as described by the Mie theory.

As noted hereinabove, prior art approaches have attempted to measure wear debris concentrations through simple transmission or absorption measurements. This approach is subject to significant error, however, as the plots of FIG. 3 illustrate.

Figure 3:
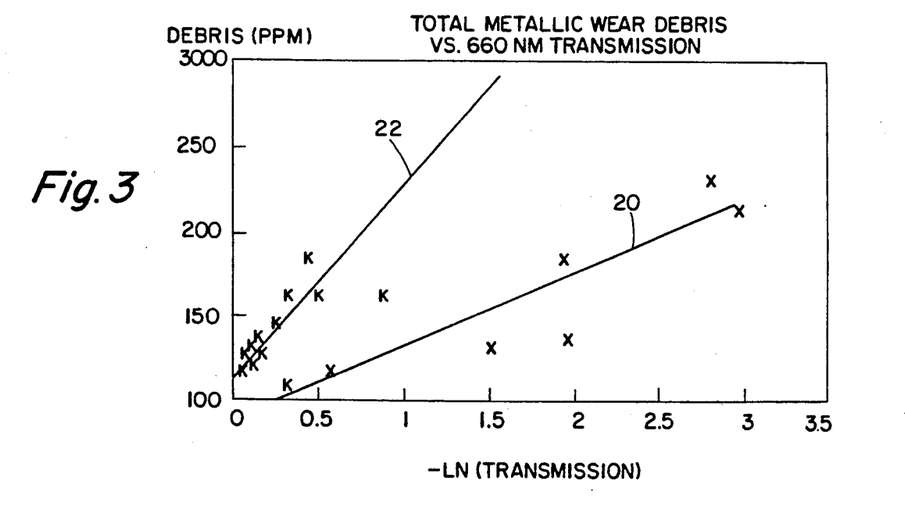
FIG. 3 is a plot depicting total wear debris measured by atomic absorption spectroscopy as a function of the natural log of 660 nm (red) light transmission through a plurality of used motor oil samples.

More particularly, FIG. 3 is a plot of data based on a plurality of samples of used motor oils taken from various engines. Total wear debris content of the oil as measured by atomic absorption spectroscopy is plotted on the vertical axis as a function of the natural log of transmission of a single light source along the horizontal axis, in this particular example a 660 nm (red) light source. In FIG. 3, the data points designated as "k" are from motor oils in automotive engines primarily fueled with natural gas (a low carbon fraction fuel), and the data points designated "x" are from engines using a mixture of gasoline and natural gas. As represented by distribution lines 20 and 22, there are two distributions of data, the gasoline engine oils (distribution line 20) having much higher extinction levels for a given level of debris than the natural gas engines (distribution line 22). A conclusion to be drawn is that something other than metallic wear debris is extinguishing the light in engines using the higher carbon fraction fuel, and this "something other" is most likely carbon particles which cannot be measured by atomic spectroscopy in a carbon-based oil.

Figure 4:
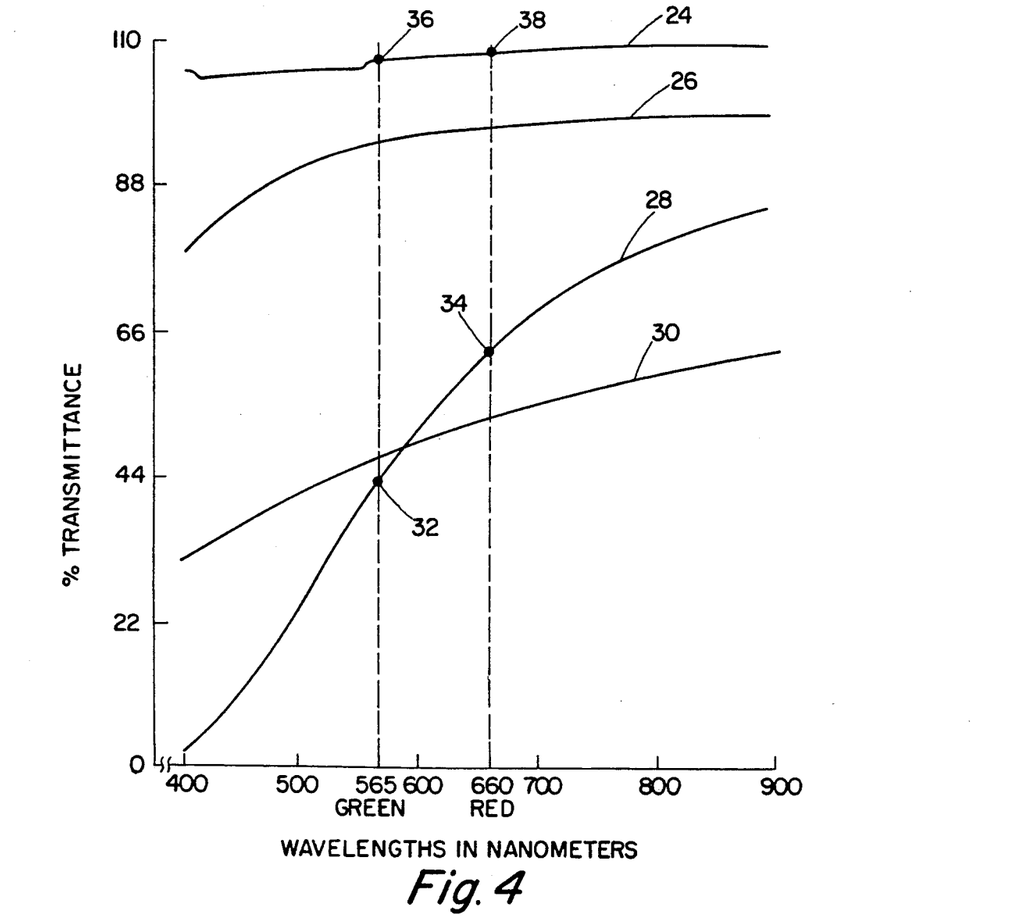
FIG. 4 includes four plots of transmission spectra of oil in various conditions, plotting percent transmittance as a function of wavelength.

The present invention employs an optical spectrometry technique, and it is accordingly relevant to consider the spectral characteristics of motor oils in various conditions. FIG. 4 plots transmission spectra of various oil samples employing a Beckman Model DU-65 Spectrophotometer. The vertical axis is in units of the percent of the light transmitted relative to a reference, while the horizontal axis is wavelength in nanometers, with two points, 565 nm (green) and 660 nm (red) particularly indicated for purposes of illustration.

In FIG. 4, line 24 is a transmission spectrum of a common SG grade SAE 10W-40 motor oil relative to air through a 125 micron path. (The amount of light transmitted is actually greater with fresh oil in the sample holder than when it is filled with air because the oil more closely matches the refractive index of the sample holder.) Fresh, high-quality automotive motor oils have similar optical characteristics. They tend to transmit red and near-infrared light well, while scattering shorter wavelength blue and violet light. In bulk oil samples this results in a typical reddish-amber color when the light is viewed through the oil (transmission), and a bluish-green color seen when the oil is viewed at right angles to the light path (scattering). Thus, from plot line 24 it can be seen that, as wavelengths decrease from near-infrared (900 nm) to violet (400 nm), slightly less light is transmitted.

As oil is exposed to localized high temperatures in an operating engine, its chemical structure begins to change as a result of oxidation and thermal decomposition. During the process, there is a general tendency towards a darkening and thickening of the oil. This effect is much more pronounced at shorter wavelengths than at longer wavelengths. Thus, line 26 plots the transmission spectrum of a new 10W-40 oil which was partially "oxidized" by exposure to high temperatures in the presence of air. (This spectrum is relative to the same oil when unoxidized based on transmission through a 125-micron path.) Almost all of the infrared radiation is still transmitted, while only 77% of the violet light passes through the oil. The oil appears to be a murky brown color to the eye.

This change in optical properties is partially reversible by filtering the oil through a 0.20 micron filter. This indicates that at least a portion of the oxidation process and its optical effects involve a buildup of discrete, light scattering particles (or large polymer structures) with dimensions on the order of 200 nm or larger.

These observed changes are also consistent with the known quantum effect of increased length in organic molecules, an increase in the number of possible energy states for the bonding electrons with a corresponding decrease in transition energies. Or, simply stated, increasing wavelengths (lower energy levels) of peak light absorption occur with increasing molecular size.

As oil continues to degrade, by-products of combustion and wear solids begin to accumulate along with the oxidation products in the oil. As the concentration of particles increases, the oil's overall ability to transmit light decreases. But more importantly, the slope of the transmission curve also increases.

Thus, line 28 is a transmission spectrum of a sample of used motor oil from a gasoline and natural-gas-fueled engine known to contain 225 parts per million (ppm) of metallic wear debris. It is significant that slope of the transmission curve has drastically increased with the buildup of particulates. Interestingly, attempts to filter the contaminated oil through a 0.2 micron filter failed. The filter did not pass the contaminated oil, showing that a significant increase had occurred in the particle population at, or above, the 200 nm size.

Line 30 in FIG. 4 is a spectrum of oil taken from a diesel engine and diluted with fifty parts of fresh motor oil. Because of the dilution, metal wear debris was less than a few parts per million. Organic insolubles were also diluted to near that of new oil as evidenced by the soot-laden oil's ability to pass the 0.20 micron filter.

A characteristic of diesel combustion is the production of spherical carbon particulates (soot) in the size range of 10 to 30 nm which tend to agglomerate in the form of branched chains and rings. These are elemental carbon particulates as opposed to carbohydrates. Although the precise concentration of carbon is unknown in this sample, the relative spectral effect of the carbon particulates can be observed. Although the oil extinguishes as much light overall as an oil containing wear particles, the spectral characteristics are much more uniform, with a very gradual slope. Considering the broadband extinction characteristics of carbon soot, this is not surprising.

This observed phenomenon as represented by lines 28 and 30 of FIG. 4 can be explained by applying the Mie scattering theory to the problem of spherical carbon particulates versus the extinction characteristics of metal spheres. The correspondence between observation and theory is not absolute, inasmuch as the observed differences in slope between the spectra represented by lines 28 and 30 is more pronounced than is predicted by theory. This is probably due to the fact that this application of the theory can only approximate the highly complex structure of real world soot microstructures with an assumed spherical shape.

In addition to measurements of metallic wear debris contamination, laboratory measurements have determined there is a direct correlation between readings taken with an instrument in accordance with the invention and oil viscosity increases in experiments in which the oil was thermally degraded in the laboratory. It is believed the instrument is responding to large polymer buildup in lubricating oil i.e., increasing the average molecular weight of the oil.

An important aspect of the invention is to provide a practical technique for rapidly evaluating variation in transmittance as a function of wavelength, i.e. the slope of the transmission spectra as depicted in FIG. 4. It has been discovered that optically measuring transmittance at two distinct wavelengths within the wavelength range of interest is sufficient, for example, at points 32 and 34 in FIG. 4. Thus, point 32 represents transmittance at a wavelength of 565 nm (green light), while point 34 represents transmittance at a wavelength of 660 nm (red light), through the sample oil with 225 ppm metallic wear debris contamination. In one approach to measurement, the ratio of transmittance at the shorter of the two distinct wavelengths, in this example 565 nm (green light), to transmittance at the longer of the two distinct wavelengths, in this example 660 nm (red light), indicates the amount of metallic wear debris contamination, decreases in the ratio from a ratio of unity indicating increasing contamination, or decreasing lubricating oil quality. Thus, by comparison, if transmission measurements are made of clean oil (line 24) at the same two distinct wavelengths, points 36 and 38 result, and the ratio of green to red light transmission is nearly unity.

From FIG. 4, it will be appreciated that the particular two distinct wavelengths at which transmission measurements are taken are not critical. Moreover, the 900 nm upper limit in the plot of FIG. 4 can be extended well into the near-infrared, up to, for example, 1300 nm. Successful results have been obtained using the following wavelength pairs: 565 nm green with 700 nm red; 660 nm red with 880 nm infrared; 440 nm blue with 700 nm red; and 660 nm red with 940 nm near-infrared. The 660 nm/940 nm pair has been found to have better sensitivity to water contamination. It is believed that the principle of the invention is applicable at least in the approximate wavelength range of from 300 nm to 1300 nm. However, it may be noted that, at this time, the wavelength range for which nearly continuous experimental data is available is 400 nm to 940 nm. On the basis of presently-available data, the existence of anomalies in the wider wavelength range cannot be ruled out, but none are expected.

Figure 5:
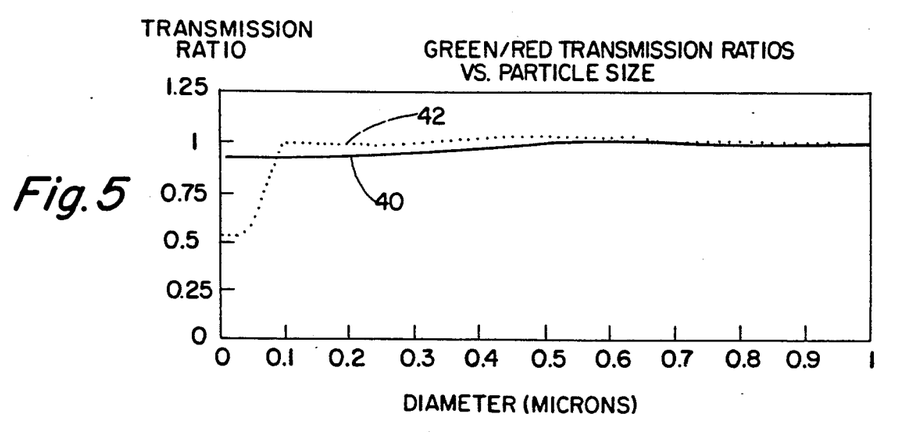
FIG. 5 includes two plots of calculated green/red transmission ratios as a function of particle size for carbon and iron particles, respectively.

Also relevant to consider in the context of the invention is the effect of particle size. FIG. 5 plots data generated with a computer model based on Mie and Rayleigh extinction. The vertical axis is the transmission ratio of 565 nm (green) light to 660 nm (red) light radiation plotted as a function of particle size along the horizontal axis. In particular, solid line 40 plots carbon extinction as a function of diameter, while dotted line 42 plots iron extinction as a function of particle diameter. In both cases, particle concentration is 200 ppm by volume.

The significance of FIG. 5 is that, in the range below 0.1 micron, which encompasses the size distribution of carbon particulates in used motor oils, the transmission ratio for carbon is significantly higher than for iron. This is primarily due to the fact that carbon is a good absorber of light and a poor scatterer. By contrast, the metals both scatter and absorb light at these wavelengths. Thus, a green/red ratio measurement is relatively insensitive to the presence of carbon particulates under 0.1 micron, while remaining sensitive to small metal particles.

Calculated plots comparing transmission ratios of other metals to carbon, such as copper to carbon, lead to similar conclusions.

The practical significance of all of this is that by using ratios rather than absolute transmission values, it is possible to approximately measure wear and oxidation debris particle concentrations by simple optical sensors in the presence of moderate concentrations of carbon soot. This distinction between soot and other particles is important because the presence of well-dispersed, small soot particles does not necessarily indicate a degraded oil. The soot particles, which will easily pass through a 0.20 micron filter, are too small to be mechanically significant in most engine oil films which may range from 0.5 microns on cam/follower surfaces to 20 microns or more in journal bearings. Typically, soot only presents a lubrication problem in compression ignition (diesel) engines where very high concentrations may lead to agglomeration and filter clogging.

Figure 6:
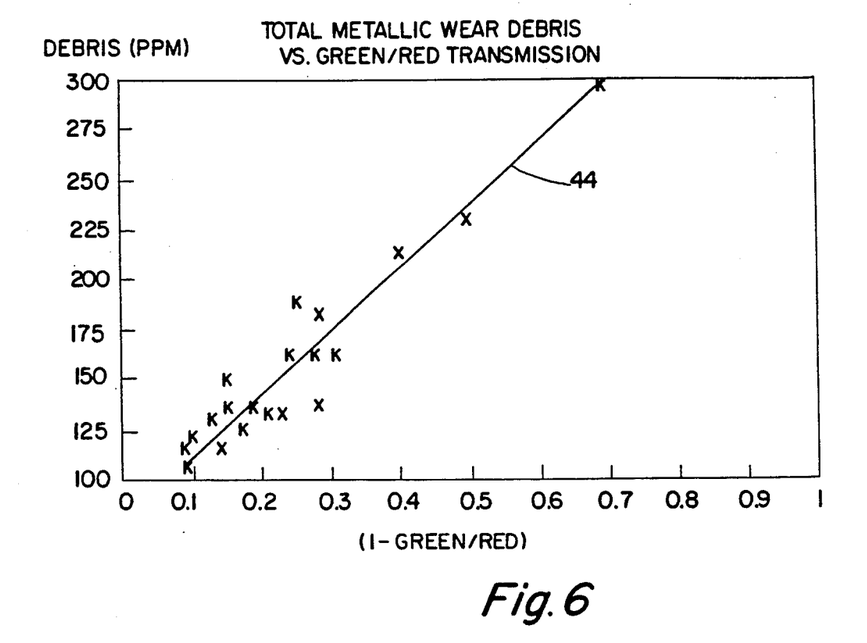
FIG. 6 is a plot, which may be contrasted to FIG. 3, of total metallic wear debris measured by atomic absorption spectroscopy as a function of the ratio of 565 nm (green) to 660 nm (red) light transmission through samples of motor oil.

With the foregoing analysis as background, reference may be made to FIG. 6, which depicts actual results in accordance with the invention. Evident is a close correlation between green/red ratio measurements and the results of atomic absorption spectroscopy. More particularly, FIG. 6, which may be contrasted with FIG. 3 (which shows the results of measurements at a single wavelength and is of the very same oil samples), well illustrates that the green/red ratio measurement is relatively insensitive to the presence of small (under 0.1 micron) carbon particulates, while remaining sensitive to small metal particles. Again, the data points designated as "k" are from motor oils in automotive engines which were primarily fueled with natural gas, a low-carbon-fraction fuel, while the points marked "x" are from engines using a mixture of gasoline and natural gas. In FIG. 6, scatter is significantly eliminated from the data, and data points concentrate around a single distribution line 44.

From the foregoing, it can be concluded that the techniques of the invention are capable of detecting metal wear debris in the presence of high levels of carbon (and also capable of detecting carbon). Moreover, the technique is sensitive to a wide range of particle sizes (unlike an atomic spectrometer).

Figure 7:
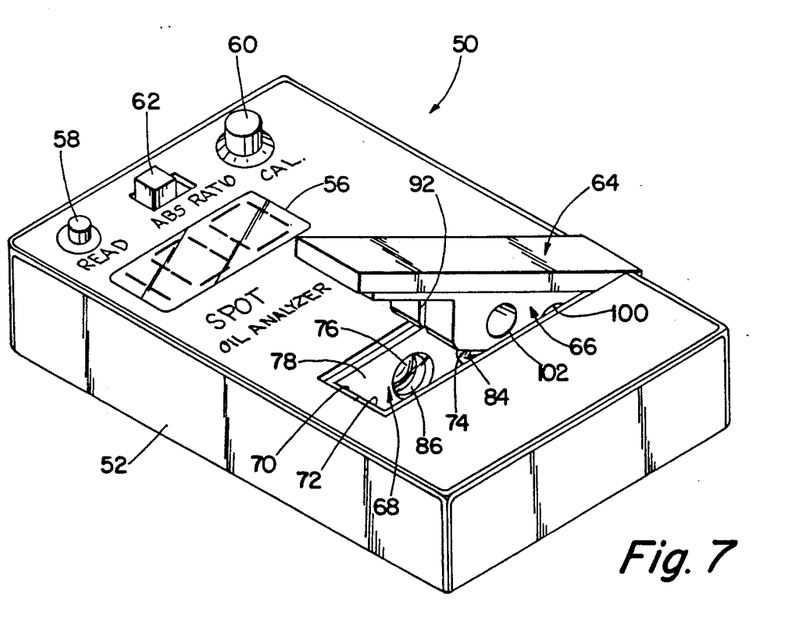
FIG. 7 is a three-dimensional view of a spectral portable oil tester (SPOT) instrument in accordance with the invention.

Referring now to FIG. 7, depicted is a practical hand-carried, battery-powered instrument 50 termed a spectrometric portable oil tester (SPOT) for use in testing used motor oils from reciprocating engines. In overview, and in accordance with the foregoing, the principle of operation is the measurement of the ratio of transmission of light radiation at two wavelengths, for example 565 nm (green) and 660 nm (red). Several drops of oil are placed on a "dual-path" sample holder (described with reference to FIGS. 10-14 hereinbelow) which is, in turn, placed in the instrument 50. The light transmitted through the samples is measured as a conductance by a pair of cadmium-sulfide photoconductors, one in each path. The ratio of the conductances, which is roughly proportional to the ratio of the transmitted green and red light, is output to the user.

The instrument 50 will also read the absolute green transmission value. This value may be used to estimate the carbon loading of oil, particularly when the green/red ratio measurement indicates a lack of significant metallic wear debris contamination, and to ensure that the instrument is being operated within a reasonable transmission range. Calibration for either ratio or absolute measurement is made by adjusting the instrument to read 100% with a sample of fresh oil, or with an appropriate amber calibration filter.

The instrument 50 can also be applied to all non-opaque lubricating oils, including motor oils, transmission fluids, light gear oils, and hydraulic fluids. Because the instrument measures wear debris concentrations, it can be used for detecting abnormal wear of oil-wetted machinery surfaces.

Considering the instrument 50 in detail, an instrument case 52 includes a front panel 54 presenting a digital display readout 56, a "READ" push button switch 58, a "CALIBRATE" knob 60, and an "ABSOLUTE/RATIO" slide switch 62 for selecting mode of operation. A hinged sample door assembly 64 includes a suitable sample holder guide 66, and is received within a cavity 68 within which are measuring elements. When the sample door assembly 64 is closed, ambient light is excluded from the interior of the cavity 68.

Figure 8:
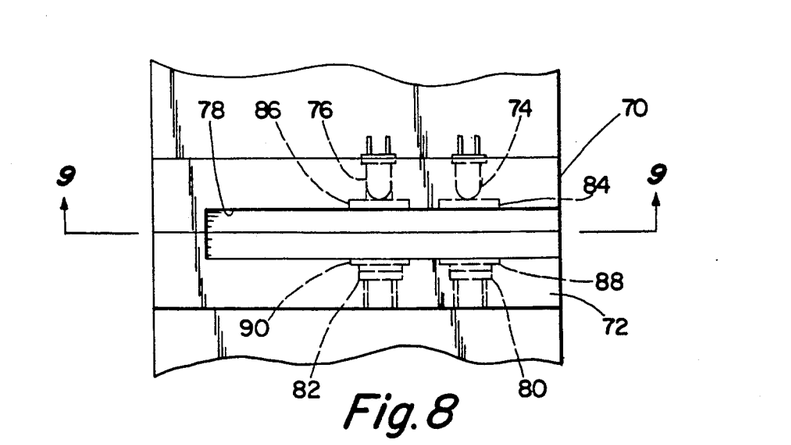
FIG. 8 is a plan view of a portion of the FIG. 7 instrument depicting a sample cavity and the positioning of a pair of light-emitting elements and a corresponding pair of photoconductive light sensors.
Figure 9:
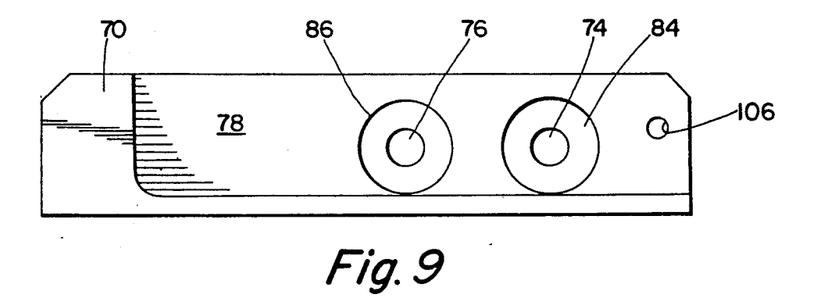
FIG. 9 is a view along line 9—9 of FIG. 8 from within the sample cavity.

FIG. 8 is a view down into the cavity 68, and schematically illustrates an LED holder 70 and a corresponding photodetector holder 72, each formed of a suitable opaque, black plastic material. FIG. 9 is a view from within the cavity 68 towards the LED holder 70. The view in the opposite direction, that is towards the photodetector holder 72, is similar, although not shown. The LED holder 70 supports, midway down, respective red and green light-emitting diodes 74 and 76 (shown in phantom in FIG. 8) received in apertures perpendicular to a cavity sidewall 78. The photodetector holder 72 supports, midway down, corresponding photodetectors in the form of cadmium-sulfide (CdS) photoconductors 80 and 82 in a similar manner. A pair of light paths are thus established across the cavity 68.

The instrument of the invention uses diffused rather than coherent light because wear particulates typically have non-spherical geometries. Diffusion of light ensures that light is extinguished as a function of particle surface areas both normal and parallel to the axis of the light path. This is in contrast to instruments which have a well-focused light path intended to measure an optical cross-section or silhouette. Thus, the light path is not focused; rather, it is broad, incoherent, and scattered.

Accordingly, to serve as diffusers, colored, frosted plastic lenses 84 and 86 are placed over the LEDs 74 and 76, and colored, frosted plastic diffusers 88 and 90 are likewise placed over the photodetectors 80 and 82. The diffusers preferably are all colored to match the corresponding LED 74 or 76.

Figure 10:
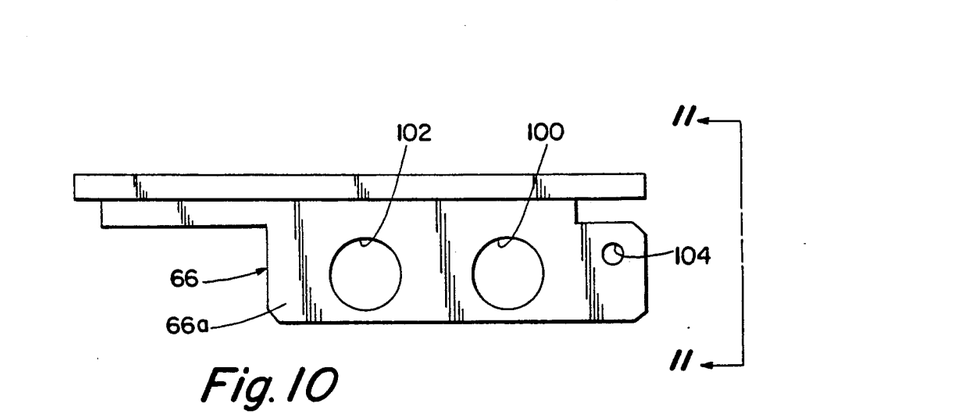
FIG. 10 is a side elevational view of the sample door assembly of the FIG. 7 instrument.
Figure 11:
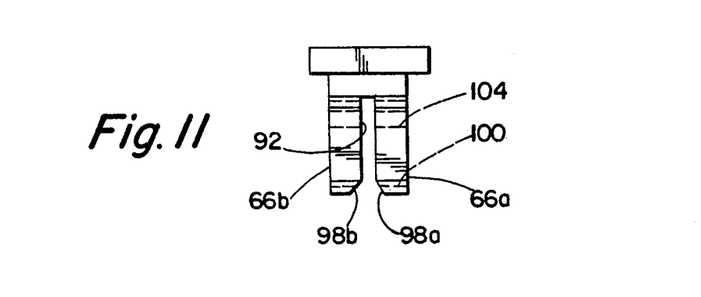
FIG. 11 is an end view taken along line 10—10 of FIG. 9.

FIGS. 10 and 11 show further details of the sample door assembly 64 and sample holder guide 66. The sample holder guide 66 more particularly comprises a pair of depending parallel portions 66a and 66b separated by a slot 92 for receiving a sample holder either of the form 94 as described hereinbelow with reference to FIGS. 12 and 13 or of the form 96 as described hereinbelow with reference to FIG. 14. Chamfers 98a and 98b facilitate insertion of the sample holder 94 or 96.

To allow light to pass from the LEDs 74 and 76 through an oil sample to the photodetectors 80 and 82 when the sample door assembly 64 is closed, the portions 66a and 66b of the sample holder guide 66 include suitably-positioned apertures 100 and 102. Another, smaller aperture 104 serves as a pivot point and receives a pivot pin (not shown) at one end engaging an aperture 106 in the FIG. 9 LED holder 70. Opposite the aperture 106 is a corresponding aperture (not shown) in the photoconductor holder 72.

Figure 12:
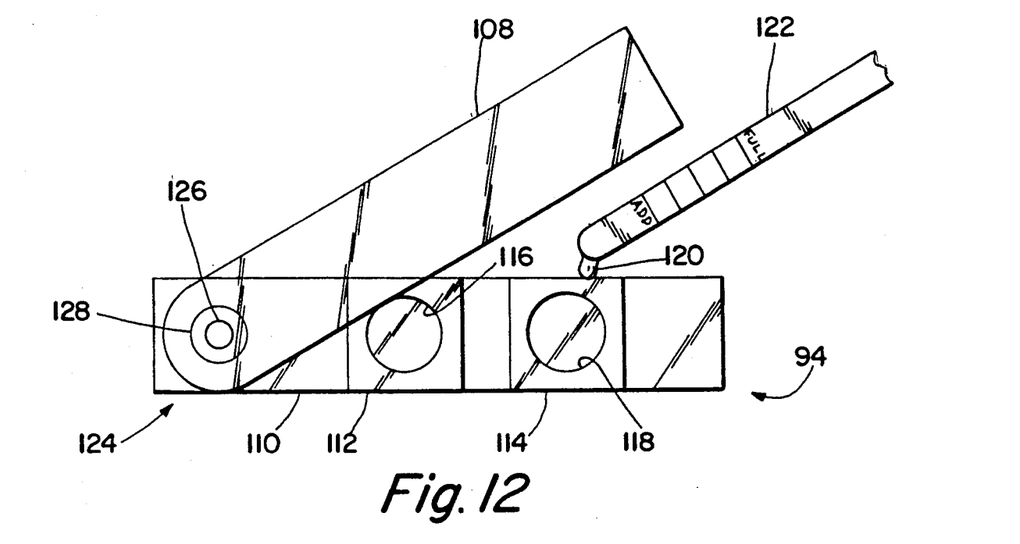
FIG. 12 is a plan view depicting one form of sample holder in accordance with the invention.
Figure 13:
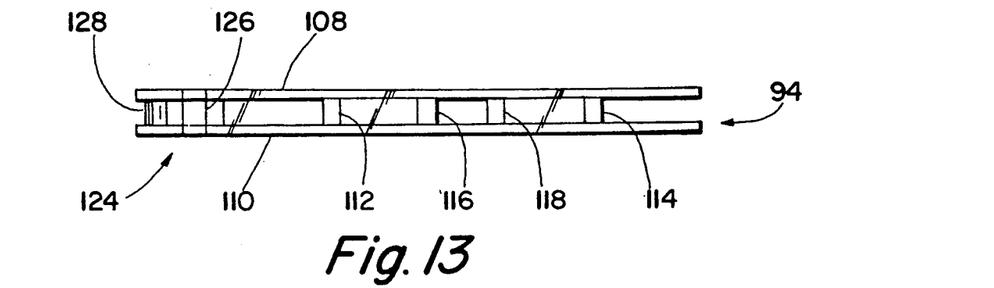
FIG. 13 is a side view of the FIG. 11 sample holder.

FIGS. 12 and 13 depict one form of sample holder 94. The sample holder 94 includes a pair of light-transmitting plastic strips 108 and 110 facing each other and spaced apart by black, opaque spacers 112 and 114 having respective apertures 116 and 118. The plastic strips 108 and 110 can be either frosted or clear, but in either event are light transmitting.

Illustrating actual use, a representative oil drop 120 from a dipstick 122 is deposited into the cavities thus defined by the apertures 116 and 118. The strip 108 is then closed over the strip 110. The thickness of the oil sample is controlled by the thickness of the spacers 116 and 118, thus ensuring uniform sample volume and thickness. Opposing surfaces between the plastic strips 108 and 110 are well sealed, and the opaque spacers 112 and 114 prevent light scattering from one light path to the other.

In the particular form of sample holder 94 shown in FIGS. 12 and 13, the plastic strips 108 and 110 are pivoted at point 124 by means of a pivot pin 126 and a pivot spacer 128. As an alternative, a single piece of plastic strip can be simply folded at point 124 to form two segments 108 and 110.

Figure 14:
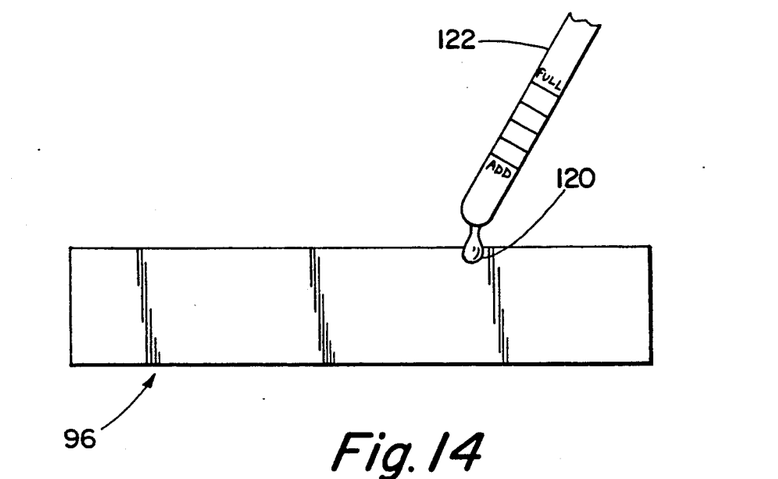
FIG. 14 depicts another form of sample holder in accordance with the invention, namely a cellulose matrix.

Another form 96 of sample holder is depicted in FIG. 14, and comprises simply a cellulose matrix (absorbent paper) on to which oil drops 120 are placed from the dipstick 122. Use of the cellulose matrix sample holder 96 aids in diffusing the light to the oil sample, and is also effective in providing a thin-film optical path.

It will be appreciated that either the plastic strip sample holder 94 or the cellulose matrix sample holder 96 is placed in the slot 90 (FIGS. 7 and 11) of the sample holder guide.

Figure 15:
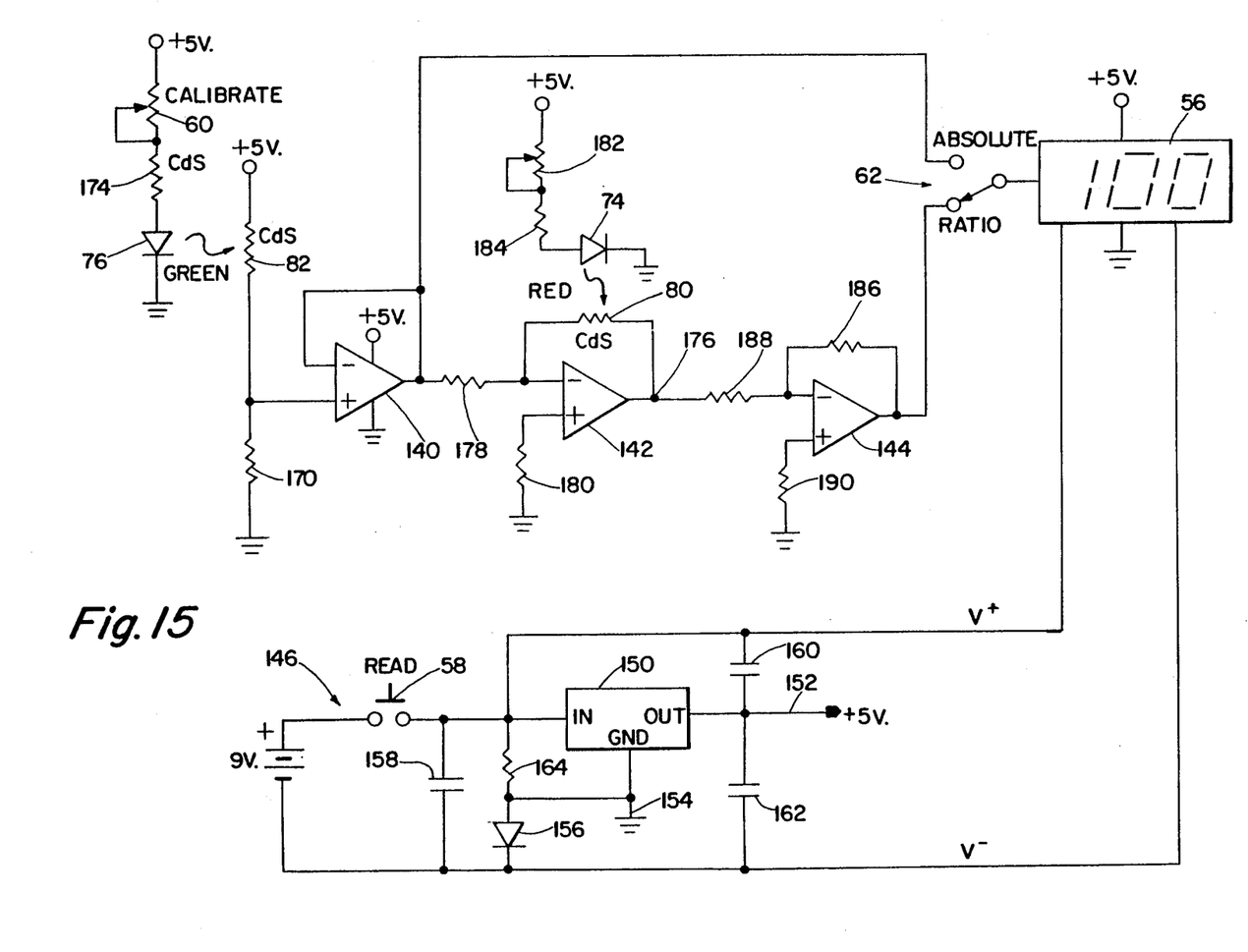
FIG. 15 is an electrical schematic diagram depicting circuitry for the FIG. 7 instrument.

FIG. 15 is an electrical schematic diagram of suitable battery-powered circuitry for inclusion in the instrument 50. In overview, FIG. 15 circuit includes three operational amplifier (op-amp) stages 140, 142 and 144, which may all be included within a single type number LM324 integrated circuit package operated from a single +5 volt DC source.

Included in the FIG. 15 circuit are the two cadmium-sulfide photoconductors 80 and 82. While the specific values of the CdS photoconductors 80 and 82 are not critical, they should be matched. CdS cells are not specified by asolute resistance values for a given incidence of light radiation, but, rather, by a well-defined slope and an offset range, typically 10K ohms to 40K ohms. The assembly process involves testing individual cells to find pairs with nearly identical offsets. Suitable cells are Radio Shack catalog number 276-1657.

Also included is a common power supply section, generally designated 146, operated from a 9 volt battery 148 connected to the rest of the circuitry through the "READ" push button switch 58.

Within the power supply section 146, a 5 volt three-terminal voltage regulator 150 is employed in a configuration which provides a regulated +5 volts on line 152 with reference to ground 154, a slightly higher voltage on line V+ for supplying the digital display circuitry 56, and a negative voltage along line V−. The V− voltage is negative with reference to ground 154 by an amount equal to the forward voltage drop through a light-emitting diode 156, which may also serve as a pilot light. The power supply section 146 is otherwise conventional in configuration, including a 33 mfd capacitor 158 at the input following the "READ" push button switch 58, and 0.1 mfd stabilizing capacitors 160 and 162 between the outputs. A 390 ohm 164 resistor is connected from the switch 58 to forward bias the LED 156.

Considering now the active portion of the FIG. 15 circuit, the CdS photoconductor 82 which receives light from the green LED 76 is connected in voltage divider configuration with a 2K ohm series resistor 170 and to the non-inverting (+) input of the first operational amplifier 140, which is configured as a unity-gain, high-input impedance buffer amplifier, having an output 172.

The green LED 76 is supplied from the +5 volt source through the calibration control 60, which comprises a 200 ohm variable resistor, in series with a 300 ohm fixed resistor 174.

Light sensed by the photoconductor 82 is accordingly light from the green LED 76 after it has passed through the oil sample. In operation, the voltage output 172 of the first operational amplifier stage 140 increases with increasing levels of light sensed by the photoconductor 82.

The second operational amplifier stage 142 is configured as an inverting amplifier with variable feedback and accordingly variable gain. More particularly, the photoconductor 80 which receives light from the red LED 74 comprises a negative feedback path between the output 176 of the operational amplifier 142 and its inverting (−) input. The photoconductor feedback resistor 80 cooperates with a 2K ohm input resistor 178 to establish the gain of the operational amplifier stage 142. A 5K ohm resistor 180 connected between the operational amplifier 142 non-inverting (+) input and circuit ground establishes a reference input.

The red LED 74 is similarly energized from the +5 volt supply through a 200 ohm variable resistor 182, adjusted during manufacture, and a fixed 200 ohm resistor 184. Light sensed by the photoconductor 80 is accordingly light from the red LED 74 after it has passed through the oil sample. In operation, an increase in conductance of photoconductor 80 caused by an increase in red light transmitted through the oil sample results in a decrease in the gain of the second operational amplifier stage 142.

The third operational amplifier stage 144 is configured simply as a unity-gain invertor, and accordingly has identical 10K ohm feedback 186 and input 188 resistors connected to the inverting (minus) input. Reference is established by a 5K ohm resistor 190 connected from the non-inverting (+) input to ground.

This circuitry accordingly provides a simple and straightforward approach to indicating the ratio of green to red light transmission through the oil sample. The output of the circuit is approximately proportional to the conductance of the photodetector 82 receiving the green light to the conductance of the photoconductor 74 receiving the red light.

For display output to the user, the output of the third operational amplifier stage 144 is connected through the mode switch 62 when in its "RATIO" position to the input of the digital display 56, which may comprise for example a conventional digital volt meter including an ICL7136 integrated circuit connected to a type number LCD002 digital display.

In order to make absolute readings of green light transmission, the mode switch 62 has an ABSOLUTE position, whereby the input of the digital display volt meter 56 is connected to the output 172 of the first operational amplifier stage 140.

In use, with a calibration sample of fresh oil in the sample holder 94 or 96, the intensity of the green LED 76 is varied by means of the calibration resistor 60 to produce a nominal reading of 100 on the digital volt meter display 56. Next, the sample to be tested is placed in the instrument. Typically, the used oil sample will pass less green light than red light. This creates a higher value of resistance in photoconductor 82 compared to photoconductor 80, causing the reading to decrease below 100 proportional to the ratio of transmitted green light relative to transmitted red light.

The ease of operation and performance characteristics of the instrument of the present invention are further illustrated by the following excerpts from the instruction manual:

Calibration

The spectral portable oil tester (SPOT) should be calibrated before use. This is a simple procedure which varies slightly with the sample delivery technique. (In one version the used oil is placed in a plastic sample holder which is placed in the instrument. In the other version a paper tab replaces the plastic sample holder.)

Plastic Sample Holder Calibration

1. Open the sample door and insert the plastic sample tab into the slot in the bottom of the door. The tab should rest against the stop at the hinged end of the door and rest flush along the door. Before closing the door check to make sure that the sample windows in the tab are aligned with the circular holes in the sample door.

2. Check to make sure that the ABSOLUTE/RATIO slide switch is in the RATIO position (toward the right).

3. While holding the READ button down, adjust the CALIBRATION knob until the instrument displays a value of 100. Continue to hold the READ button down for five seconds to ensure that the electronics have settled.

4. Remove the sample tab from door and insert the amber filter in the sample tab so that it fully covers both windows. Replace the sample tab in the sample door making sure that trimmed corner faces away from the top of the door and that the sample tab is firmly in place. Press the READ button and allow five seconds for the electronics to settle. The instrument should in read in the range of 84 to 88.

NOTE: If the reading is not within the specified range, check to make sure that the sample tab is placed properly and that the amber filter fully covers both sample windows. Check the clear lenses on both sides of the inside of the sample door slot for oil or dirt. Wipe clean with a soft tissue paper if necessary.

Do not use an instrument which fails the calibration routine.

Calibration with a Paper Sample Tab

1. Place the pale amber filter in the sample door so that it blocks both windows.

2. Check the position of the ABSOLUTE/RATIO slide switch. It should be in the RATIO position (to the right).

3. While holding the READ button down, adjust the CALIBRATION knob until the instrument displays a value of 100. Wait five seconds for the electronics to settle before releasing the READ button.

4. Remove the pale amber filter and replace with the grey-brown filter. Check the open sample door to ensure that both windows are covered by the filter. Close the door and depress the READ button. After five seconds the instrument should read in the range of 83 to 87.

NOTE: If the reading is not within the specified range, check to make sure the filters fully cover both sample windows. Check the lenses in both sides of the inside of the sample door slot for oil or dirt. Wipe clean with a soft tissue paper if necessary.

Do not use an instrument which fails the calibration routine.

Testing with SPOT

SPOT is sensitive to oxidation of motor oils and sub-micron-sized wear debris. It is relatively insensitive to normal levels of soot in reciprocating engines fueled with natural gas and gasoline. SPOT should not be used with heavily sooted used oils from diesel engines.

Use with Plastic Sample Tabs

1. If the instrument has not had a calibration check just prior to use, make the check.

2. Clean the plastic sample tab with a clean, soft tissue paper and place a drop of oil in each of the windows.

3. Remove excess oil by wiping the closed sample tab with a clean, soft tissue paper.

4. Open the sample door, insert the tab, close the door, and depress the READ button. After five seconds, record the value shown in the display. During the reading sequence, lightly press down on the sample door to ensure that it is fully closed.

5. Move the ABSOLUTE/RATIO slide switch to the left to make an absolute reading. An absolute reading below 20 indicates that the oil is badly contaminated with carbon and that an accurate SPOT reading cannot be taken. This should only occur with used oils from diesel engines.

6. Remove sample tab and wipe clean.

The TABLE below gives approximate break points for SPOT analysis. SPOT readings correlate closely with results of Atomic Spectral Oil Analysis. This laboratory testing method is used to measure the elemental wear debris content of used motor oils. Neither SPOT nor Atomic Spectral Analysis is sensitive to large debris particles resulting from causes other than normal lubricating oil degradation.

When SPOT readings are lower than 80, an oil change is indicated as the oil is beginning to oxidize and the rate of wear is increasing. However, one should never prolong oil change interval beyond the engine manufacturer's recommended oil change interval as doing so may invalidate the new engine warranty. In average stop and go service, following extended oil change intervals of 5,000 miles or more will significantly shorten engine life.

TABLE

| SPOT VALUE (Ratio) | Recommended Actions | |
|---|---|---|
| | APPROXIMATE WEAR DEBRIS LEVEL (ppm Fe) | ACTION |
| 80 to 100 | <35 | NONE** |
| 50 to 79 | 35 to 60 | CHANGE OIL |
| <50 | >60 | TAKE SAMPLE FOR FULL LAB ANALYSIS - CHANGE OIL |

**Do not exceed manufacturer's recommended oil change interval.

Use with Paper Sample Tabs

1. If the instrument has not had a calibration check just prior to use, make the check.
2. Coat a clean paper sample tab with the used oil. Allow about thirty seconds for the oil to saturate the paper and then wipe off the tab with a clean, soft tissue paper.
3. Open the sample door, insert the tab, close the door, and depress the READ button. After five seconds record the value shown in the display. During the reading sequence, press down lightly on the sample door to ensure that it is fully
4. Move the ABSOLUTE/RATIO slide switch to the left to make an absolute reading. An absolute reading below 10 indicates that the oil is badly contaminated with carbon soot and that an accurate SPOT reading cannot be taken. This should only occur with used oils from diesel engines.
5. Dispose of the used tab. It cannot be reused.
6. Refer to the TABLE for a recommended action.

Finally, there are several limitations of the technique of the invention, which are summarized here.

As previously noted, soot (very fine carbon particles) in an oil will absorb light. In diesel engines operated at high loads with worn rings, soot may be present in the oil in very high concentrations. Visible light will only propagate a few microns in such oils and optical oil analysis methods cannot be applied. In addition, although the extinction characteristics of carbon soot are relatively flat, they are not perfectly so. Therefore, the testing technique of the invention should not be applied to heavily-sooted oils.

The method of the invention is based primarily on an assumption that wear occurs as a result of lubricating oil oxidation and/or that the active wear mechanisms result in an increase of the fine particle concentrations. Above a particle size of about 0.5 microns, extinction is no longer wavelength-dependent for visible light. In reciprocating engines oil degradation/contamination is the most common cause of wear. In addition, most of the wear involves mild adhesive, abrasive, or erosive wear mechanisms acting on well-machined surfaces with sub-micron asperities. When larger particles occur, they tend to be reduced in size by abrasive mechanisms. However, the method should not be employed as a condition monitoring tool in other machinery types where severe wear may occur without oil degradation or the production of fine wear debris.

From the foregoing, it will be appreciated that the invention is based on a recognition that the spectral characteristics of motor oils change with the buildup of sub-micron particulates (and larger organic molecules) in the oil. These characteristics correlate well with an oil's ability to lubricate small automotive engines as evidenced by wear debris analysis. An extremely close correlation was found between wear debris as measured by atomic spectrometry and simple optical transmission ratios of light from a pair of sources of two distinct wavelengths in used motor oils. The invention may readily be embodied in an inexpensive instrument which can be used to detect degraded motor oil in small natural gas and gasoline-fueled engines.

While specific embodiments of the invention have been illustrated and described herein, it is realized that numerous modifications and changes will occur to those skilled in the art. For example, a variety of circuits may be employed, including circuits which are primarily digital, to compare the transmittances at two wavelengths, or to perform a more complex spectrum analysis involving more than two wavelengths, including computerized pattern analysis. While a simple ratio calculation is employed in the disclosed embodiment, other calculation approaches based on transmissions at two (or more) wavelengths may be employed. It is therefore to be understood that the appended claims are intended to cover all such modifications and changes as fall within the true spirit and scope of the invention.

What is claimed is:

1. An instrument for determining lubricating characteristics of oil, said instrument comprising measuring elements for optically measuring variation in transmittance as a function of wavelength as an indicator of oil lubricating characteristics, said measuring elements comprising light source means adapted to produce light at two predetermined wavelengths such that the intensity of said light at least one of predetermined wavelengths is adjustable with respect to the other and sensor means for detecting said light, said light source means and sensor means operable to optically measure variation in transmittance as a function of wavelength within an approximate wavelength range of from 300 nm to 1300 nm and said light source means and sensor means further operable to optically measure transmittance at two distinct wavelengths within the approximate wavelength range;

a calculating element connected to said measuring elements and operable to calculate the ratio of transmittance at the shorter of the two distinct wavelengths to transmittance at the longer of two distinct wavelengths as an indication of oil lubricating characteristics, decreases in the ratio from a ratio of unity indicating decreasing oil lubricating quality; and a sample delivery device for presenting a sample of oil to be measured between said light source means and said sensor means such that the amount of light reaching said sensor means depends upon the transmittance of the oil sample at a corresponding one of the wavelengths.

2. The apparatus of claim 1 further comprising diffusing means for diffusing the light for transmittance measurements including diffusors positioned between said light source means and said sample delivery device, and between said sample delivery device and said light sensor means.

3. An instrument in accordance with claim 2, wherein said means for diffusing the light comprises a cellulose matrix carrying the oil sample.

4. An instruments in accordance with claim 1, wherein said sample delivery device includes means for presenting the sampled oil for transmittance measurements as a relatively uniform thin film.

5. An instrument in accordance with claim 4, wherein said sample delivery device comprises a pair of light-transmitting plastic strips facing each other and spaced apart by spacers having respective apertures for receiving oil samples.

6. An instrument in accordance with claim 4, wherein said sample delivery device comprises a cellulose matrix carrying the oil sample.

7. An instrument for determining the metallic wear contamination of lubricating oil, said instrument comprising measuring elements for optically measuring variation in transmittance as a function of wavelength as an indicator of metallic wear contamination, said measuring elements comprising light source means adapted to produce light at two predetermined wavelengths such that the intensity of said light at least one of predetermined wavelengths is adjustable with respect to the other and sensor means for detecting said light, said light source means and sensor means operable to optically measure variation in transmittance as a function of wavelength within an approximate wavelength range of from 300 nm to 1300 nm and said light source means and sensor means further operable to optically measure transmittance at two distinct wavelengths within the approximate wavelength range;
- a calculating element connected to said measuring elements and operable to calculate the ratio of transmittance at the shorter of the two distinct wavelengths to transmittance at the longer of two distinct wavelengths as an indication of the amount of metallic wear contamination, decreases in the ratio from unity indicating increasing contamination; and
- a sample delivery device for presenting a sample of oil to be measured between said light source means and said sensor means such that the amount of light reaching said sensor means depends upon the transmittance of the oil sample at a corresponding one of the wavelengths.

8. The apparatus of claim 7 further comprising diffusing means for diffusing the light for transmittance measurements further comprising diffusors positioned between said light source means and said sample delivery device, and between said sample delivery device and said light sensor means.

9. An instrument in accordance with claim 8, wherein said means for diffusing the light comprises a cellulose matrix carrying the oil sample.

10. An instrument in accordance with claim 7, wherein said sample delivery device includes means for presenting the oil sampled for transmittance measurements as a relatively uniform thin film.

11. An instrument in accordance with claim 10, wherein said sample delivery device comprises a pair of light-transmitting plastic strips facing each other and spaced apart by spacers having respective apertures for receiving oil samples.

12. An instrument in accordance with claim 10, wherein said sample delivery device comprises a cellulose matrix carrying the oil sample.

13. A method for determining lubricating characteristics of oil, comprising: providing a calibration sample of oil; passing a first beam of light at a first wavelength through the calibration sample; passing a second beam of light at a second wavelength through the calibration sample; adjusting the intensity of at least one of the first and second beams of light with respect to the other so that the ratio of transmittance through the calibration sample of the light from the first beam as compared to the light from the second beam is unity, whereby a calibration reference is provided; providing a test sample of oil; passing the first and second beams of light through the oil; measuring the transmittance of light of the first and second beams of light through the oil; and measuring variation in transmittance of light from the first and second beams through the test sample as a function of wavelength as an indicator of oil lubricating characteristics.

14. A method in accordance with claim 13, which comprises optically measuring variation in transmittance as a function of wavelength within an approximate wavelength range of from 300 nm to 1300 nm.

15. A method in accordance with claim 14, which comprises optically measuring transmittance at two distinct wavelengths within the approximate wavelength range.

16. A method in accordance with claim 15, which further comprises calculating the ratio of transmittance at the shorter of the two distinct wavelengths to transmittance at the longer of the two distinct wavelengths as an indication of oil lubricating characteristics, decreases in the ratio from a ratio of unity indicating decreasing oil lubricating quality.

17. A method for determining the amount of metallic wear debris contamination in lubricating oil, comprising: providing a calibration sample of oil; passing a first beam of light at a first wavelength through the calibration sample; passing a second beam of light at a second wavelength through the calibration sample; adjusting the intensity of at least one of the first and second beams of light with respect to the other so that the ratio of transmittance through the calibration sample of the light from the first beam as compared to the light from the second beam is unity, whereby a calibration reference is provided; providing a test sample of oil; passing the first and second beams of light through the oil; measuring the transmittance of light of the first and second beams of light through the oil; and measuring variation in transmittance of light from the first and second beams through the test sample as a function of wavelength as an indicator of metallic wear debris contamination.

18. A method in accordance with claim 17, which comprises employing diffused light to measure transmittance.

19. A method in accordance with claim 17, which comprises optically measuring variation in transmittance as a function of wavelength within an approximate wavelength range of from 300 nm to 1300 nm.

20. A method in accordance with claim 18, which comprises optically measuring transmittance at two distinct wavelengths within the approximate wavelength range.

21. A method in accordance with claim 20, which comprises employing diffused light to measure transmittance at the two distinct wavelengths.

22. A method in accordance with claim 20, which further comprises calculating the ratio of transmittance at the shorter of the two distinct wavelengths to transmittance at the longer of the two distinct wavelengths as an indication of the amount of metallic wear debris contamination, decreases in the ratio from a ratio of unity indicating increasing contamination.

23. A method for determining the amount of contamination in lubricating oil comprising:

providing a calibration sample of oil; passing a first beam of light at a first wavelength through the calibration sample; passing a second beam of light at a second wavelength through the calibration sample; adjusting the intensity of at least one of the first and second beams of light with respect to the other so that the ratio of transmittance through the calibration sample of the light from the first beam as compared to the light from the second beam is unity, whereby a calibration reference is provided; providing a test sample of oil; passing the first and second beams of light through the oil; measuring the transmittance of light of the first and second beams of light through the oil; and measuring variation in transmittance of light from the first and second beams through the test sample as a function of wavelength as an indicator of metallic wear debris contamination; and in the event a lack of significant variation in transmittance as a function of wavelength indicates insignificant metallic wear debris contamination, optically measuring decrease in transmittance relative to a calibration sample of known clean oil at a single wavelength as an indicator of carbon particulate contamination.

24. A method in accordance with claim 23, which comprises optically measuring variation in transmittance as a function of wavelength and optically measuring decrease in transmittance at a single wavelength within an approximate wavelength range of from 300 nm to 1300 nm.

25. A method in accordance with claim 24, wherein the step of optically measuring variation in transmittance as a function of wavelength comprises optically measuring transmittance at two distinct wavelengths within the approximate wavelength range.

* * * * *

UNITED STATES PATENT AND TRADEMARK OFFICE
CERTIFICATE OF CORRECTION

PATENT NO. : 5,194,910
DATED : March 16, 1993
INVENTOR(S) : James F. Kirkpatrick, Jr.; James R. Stevenson It is certified that error appears in the above-identified patent and that said Letters Patent is hereby corrected as shown below:

Column 13, line 55

After "by" delete "asolute" and insert --absolute-- therfor.

Column 17, line 25

After "fully" insert --closed-- therefor.

Signed and Sealed this

Eighteenth Day of January, 1994

Attest:

BRUCE LEHMAN

Attesting Officer   Commissioner of Patents and Trademarks